US012625143B2

(12) United States Patent (10) Patent No.: US 12,625,143 B2
Ito et al. (45) Date of Patent: May 12, 2026

(54) X-RAY CONTRAST MEDIUM AND X-RAY IMAGE ACQUISITION METHOD

(71) Applicant: Rigaku Corporation, Tokyo (JP)

(72) Inventors: Koichiro Ito, Tokyo (JP); Naoki Kunishima, Tokyo (JP); Raita Hirose, Tokyo (JP)

(73) Assignee: RIGAKU CORPORATION, Tokyo (JP)

( * ) Notice: Subject to any disclaimer, the term of this patent is extended or adjusted under 35 U.S.C. 154(b) by 48 days.

(21) Appl. No.: 18/559,267

(22) PCT Filed: May 2, 2022

(86) PCT No.: PCT/JP2022/019493
§ 371 (c)(1),
(2) Date: Nov. 6, 2023

(87) PCT Pub. No.: WO2022/234844
PCT Pub. Date: Nov. 10, 2022

(65) Prior Publication Data
US 2024/0230658 A1 Jul. 11, 2024

(30) Foreign Application Priority Data

May 6, 2021 (JP) ................................. 2021-078340

(51) Int. Cl.
*G01N 33/58* (2006.01)
*G01N 1/30* (2006.01)
(Continued)

(52) U.S. Cl.
CPC ............. *G01N 33/582* (2013.01); *G01N 1/30* (2013.01); *G01N 23/046* (2013.01); *G01N 33/4833* (2013.01); *G01N 2001/366* (2013.01)

(58) Field of Classification Search
CPC ...... G01N 1/30; G01N 23/046; G01N 33/483; G01N 33/582; G01N 2001/366
See application file for complete search history.

(56) References Cited

U.S. PATENT DOCUMENTS 3,804,235 A * 4/1974 Anderson ................. B26F 1/02
53/413
3,981,364 A * 9/1976 Warner ................... E21B 37/02
166/174
(Continued)

FOREIGN PATENT DOCUMENTS

JP 2009-536624 A 10/2009
JP 2015-506695 A 3/2015
JP 2015-099123 A 5/2015

OTHER PUBLICATIONS

Japanese Office Action issued Mar. 18, 2025 in corresponding Japanese Patent Application No. 2023-518694, 6 pages.
(Continued)

*Primary Examiner* — Blake C Riddick
(74) *Attorney, Agent, or Firm* — XSENSUS LLP

(57) ABSTRACT

Obtaining an X-ray CT image of a biological sample includes a step of penetrating a contrast agent into the biological sample and solidifying the contrast agent to provide a contrast image of the biological sample, the contrast agent comprising wax and having a density of 0.95 $g/cm^3$ or less in its solidified state after penetration into the biological sample, and having a melting point of 40° C. to 80° C., a step of melting and resolidifying the solidified contrast agent, and a step of acquiring an X-ray CT image by irradiating the resolidified biological sample with an X ray having an energy of 4 to 12 keV, the shape of the biological sample being a shape with which a maximum optical path
(Continued)

length of the X ray in the biological sample in the step of acquiring an X-ray CT image is 2 mm or less.

11 Claims, 6 Drawing Sheets

(51) Int. Cl.

| | | |
|---|---|---|
| *G01N 1/36* | (2006.01) | |
| *G01N 23/046* | (2018.01) | |
| *G01N 33/483* | (2006.01) | |

(56) References Cited

U.S. PATENT DOCUMENTS

| | | | | | |
|---|---|---|---|---|---|
| 4,442,535 | A | * | 4/1984 | Ishijima | G01B 15/02 |
| | | | | | 378/50 |
| 5,318,767 | A | * | 6/1994 | Liversidge | A61K 49/049 |
| | | | | | 424/9.454 |
| 5,484,641 | A | * | 1/1996 | Rotter | D04H 1/64 |
| | | | | | 264/154 |
| 5,702,682 | A | * | 12/1997 | Thompson | A61K 49/0409 |
| | | | | | 424/9.42 |
| 5,719,916 | A | * | 2/1998 | Nelson | A61B 6/583 |
| | | | | | 378/207 |
| 2009/0263331 | A1 | * | 10/2009 | Wu | A61K 49/1857 |
| | | | | | 424/9.42 |
| 2010/0021389 | A1 | * | 1/2010 | Grabherr | A61P 43/00 |
| | | | | | 424/9.4 |
| 2010/0166668 | A1 | | 7/2010 | Wel et al. | |

| | | | | | |
|---|---|---|---|---|---|
| 2010/0234381 | A1 | * | 9/2010 | Parada | C12Q 1/6886 |
| | | | | | 435/7.92 |
| 2011/0008711 | A1 | * | 1/2011 | Iwahara | H01M 8/1081 |
| | | | | | 429/492 |
| 2012/0112384 | A1 | | 5/2012 | Baur et al. | |
| 2015/0031083 | A1 | * | 1/2015 | Lee | C12N 15/86 |
| | | | | | 435/69.52 |
| 2015/0315344 | A1 | * | 11/2015 | Leibler | C08F 210/02 |
| | | | | | 526/192 |
| 2016/0250013 | A1 | * | 9/2016 | Skalla | A61F 2/0063 |
| | | | | | 600/37 |
| 2017/0151764 | A1 | * | 6/2017 | Iyo | B32B 15/20 |
| 2018/0009173 | A1 | * | 1/2018 | Reuteler | B65B 7/164 |
| 2019/0031835 | A1 | * | 1/2019 | Bailey | H01M 50/414 |
| 2019/0368982 | A1 | * | 12/2019 | Schleifer | G01N 1/06 |
| 2022/0065883 | A1 | * | 3/2022 | Pedrazzini | G06V 30/1448 |
| 2022/0401587 | A1 | * | 12/2022 | Yeh | A61K 49/0419 |
| 2023/0126618 | A1 | * | 4/2023 | Mitra | G01N 1/312 |
| | | | | | 435/286.3 |
| 2024/0102932 | A1 | * | 3/2024 | Lim | G01N 1/06 |

OTHER PUBLICATIONS

Bentley et al., "Visualization of Three-Dimensional Nephron Structure With Microcomputed Tomography", The Anatomical Record, vol. 290, 2007, pp. 277-283.

Japanese Notice of Allowance issued Jun. 3, 2025 in corresponding Japanese Patent Application No. 2023-518694, 5 pages.

Chinese Office Action issued Mar. 11, 2026 in corresponding Chinese Patent Application No. 202280032318.0, 21 pages.

* cited by examiner

A

B

C

A

B

A

B

C

D

A                                    B

X-RAY CONTRAST MEDIUM AND X-RAY IMAGE ACQUISITION METHOD

CROSS-REFERENCE TO RELATED APPLICATIONS

The present application is based on PCT filing PCT/JP2022/019493, filed May 2, 2022, which claims priority from Japanese Patent Application No. 2021-078340, filed May 6, 2021, the entire contents of each are incorporated herein by reference.

BACKGROUND

Technical Field

The present disclosure relates to a method of obtaining an X-ray CT image of a biological sample, a biological sample analysis method, a contrast agent, and the like.

Description of Related Art

X-ray CT (Computed Tomography) is a technology for irradiating a subject with X rays from various directions, detecting the intensity of transmitted X rays, and combining images indicating a spatial distribution of an X-ray absorption coefficient inside the subject with a reconstruction arithmetic operation to obtain a sectional image and a three-dimensional image of the subject. With the X-ray CT, unlike an optical microscope and an electron microscope, a three-dimensional observation is possible and internal structure can be observed without breaking the subject. Therefore, the X-ray CT is used in industrial applications and various fields such as the medical field.

Micro X-ray CT currently widely spread uses a hard X-ray region with a tube voltage of approximately 50 to 160 kV. Fine and clear high image quality with strong contrast can be acquired in a subject such as a mechanical component or an electronic component configured by an element having a large atomic number. On the other hand, sufficient contrast cannot be obtained for a subject constructed from a light element having weak X-ray absorption, for example, a biological sample. Therefore, for the biological sample, the X-ray CT is performed by giving contrast with a contrast agent such as heavy metal. For example, Non Patent Literature 1 describes that an X-ray CT image of a biological sample is obtained using osmium tetroxide as a contrast agent.

CITATION LIST

Non Patent Literature

Non Patent Literature 1: MICHAEL D. BENTLEY et al., THE ANATOMICAL RECORD 290:277-283 (2007)

SUMMARY

The X-ray CT, which is widely spread today, obtains contrast depending on the level of X-ray absorption by a subject and creates an image. All of elements with low atomic numbers, for example, hydrogen, carbon, oxygen, and nitrogen, which mainly constitute a biological soft tissue, have low X-ray absorption and thus sufficient contrast cannot be obtained, and thus a high visualization capability cannot be expected in the structure of a soft tissue. Therefore, a contrast agent containing a heavy element such as osmium tetroxide is used to compensate for the low contrast. However, an appropriate contrast agent is not always present in many cases in which observation is required. In some cases, for example, the contrast agent does not sufficiently penetrate into a biological sample or the influence of the contrast agent is too strong, which has been a problem for an X-ray microscope in the observation of the biological sample.

An object of the present disclosure is, for example, to provide a method of obtaining a clear (for example, with a voxel size of 5 μm or less) high-quality X-ray CT image, for a biological sample and a contrast agent used for the method.

The present inventors have elucidated a principle of obtaining contrast in a biological sample in CT imaging and found that, by using a contrast agent comprising wax and having a density of 0.95 g/cm$^3$ or less in its solidified state after penetration into the biological sample, and having a melting point of 40° C. to 80° C., sufficient contrast can be obtained even if a contrast agent consisting of a heavy element is not used. In general, wax such as paraffin is only recognized as an embedding material used in a process of making a paraffin block as pretreatment for optical microscopy and electron microscopy. It has not been known that the wax can be used as a contrast agent.

As recognized by the present inventors, a fine and clear high-quality X-ray CT image can be obtained by a method of obtaining an X-ray CT image of a biological sample, the method comprising a step of penetrating a contrast agent into the biological sample and solidifying the contrast agent to provide a contrast image of the biological sample, the contrast agent comprising wax and having a density of 0.95 g/cm$^3$ or less in its solidified state after penetration into the biological sample, and having a melting point of 40° C. to 80° C., a step of melting and resolidifying the solidified contrast agent, and a step of acquiring an X-ray CT by irradiating the resolidified biological sample with an X ray having an energy of 4 to 12 keV, the shape of the biological sample being a shape with which a maximum optical path length of the X ray in the biological sample in the step of acquiring an X-ray CT image is 2 mm or less.

The present disclosure comprises the following embodiments.

(1) A method of obtaining an X-ray CT image of a biological sample, the method comprising:

a step of penetrating a contrast agent into the biological sample and solidifying the contrast agent to provide a contrast image of the biological sample, the contrast agent comprising wax and having a density of 0.95 g/cm$^3$ or less in its solidified state after penetration into the biological sample, and having a melting point of 40° C. to 80° C.;

a step of melting and resolidifying the solidified contrast agent; and a step of acquiring an X-ray CT image by irradiating the resolidified biological sample with an X ray having an energy of 4 to 12 keV, the shape of the biological sample being a shape with which a maximum optical path length of the X ray in the biological sample in the step of acquiring an X-ray CT image is 2 mm or less.

(2) The method described in (1), wherein the step of melting and resolidifying the contrast agent is performed in a state in which the biological sample is placed on a sample table.

(3) The method described in (1) or (2), further comprising, before the step of penetrating a contrast agent into the biological sample and solidifying the contrast agent to provide a contrast image of the biological sample, a step of cutting the biological sample into a shape with which a maximum optical path length of the X ray in the biological sample in the step of acquiring an X-ray CT image is 2 mm or less.

(4) The method described in (1) or (2), further comprising, after the step of penetrating a contrast agent into the biological sample and solidifying the contrast agent to provide a contrast image of the biological sample, a step of cutting the solidified biological sample into a shape with which a maximum optical path length of the X ray in the biological sample in the step of acquiring an X-ray CT image is 2 mm or less.

(5) The method described in (4), wherein the step of cutting the biological sample is performed with a cylindrical pipe heated to a temperature higher than the melting point of the contrast agent.

(6) The method described in any one of (1) to (5), further comprising a step of adding a marker to the biological sample, wherein in the step of acquiring an X-ray CT image, the X-ray CT image is corrected by moving slices of the X-ray CT image according to a movement of a projected image obtained from an X-ray projection image of the marker.

(7) The method described in any one of (1) to (6), wherein the contrast agent has a density of 0.95 g/cm$^3$ or less at 25° C.

(8) The method described in any one of (1) to (7), wherein the wax is solid paraffin.

(9) The method described in any one of (1) to (8), wherein the X-ray CT image is clearly obtained with a voxel size of 5 μm or less.

(10) A method of analyzing a biological sample comprising:

a step of penetrating a contrast agent into a biological sample and solidifying the contrast agent to provide a contrast image of the biological sample, the contrast agent comprising wax and having a density of 0.95 g/cm$^3$ or less in its solidified state after penetration into the biological sample, and having a melting point of 40° C. to 80° C.;

a step of melting and resolidifying the solidified contrast agent;

a step of acquiring an X-ray CT image by irradiating the resolidified biological sample with an X ray having an energy of 4 to 12 keV, the shape of the biological sample being a shape with which a maximum optical path length of the X ray in the biological sample in the step of acquiring an X-ray CT image is 2 mm or less;

a step of specifying a site to be further observed by an optical microscope and/or an electron microscope based on the acquired X-ray CT image and cutting and exposing the site;

a step of observing the site with the optical microscope and/or the electron microscope; and a step of combining the X-ray CT image and results of the observation by the optical microscope and/or the electron microscope to analyze the biological sample.

(11) A contrast agent for X-ray CT of a biological sample, the contrast agent comprising wax and having a density of 0.95 g/cm$^3$ or less in its solidified state after penetration into the biological sample, and having a melting point of 40° C. to 80° C.

According to the present disclosure, it is possible to obtain a fine and clear high-quality X-ray CT image for a biological sample.

BRIEF DESCRIPTION OF DRAWINGS

FIG. 6B: an optical microscope photograph in the case in which the paraffin was collected using the heat-treated biopsy punch. FIG. 6C: an optical photograph in the case in which the paraffin was collected using the not heat-treated biopsy punch. FIG. 6D: an optical microscope photograph in the case in which the paraffin was collected using the not heat-treated biopsy punch).

DETAILED DESCRIPTION

Figure 1:
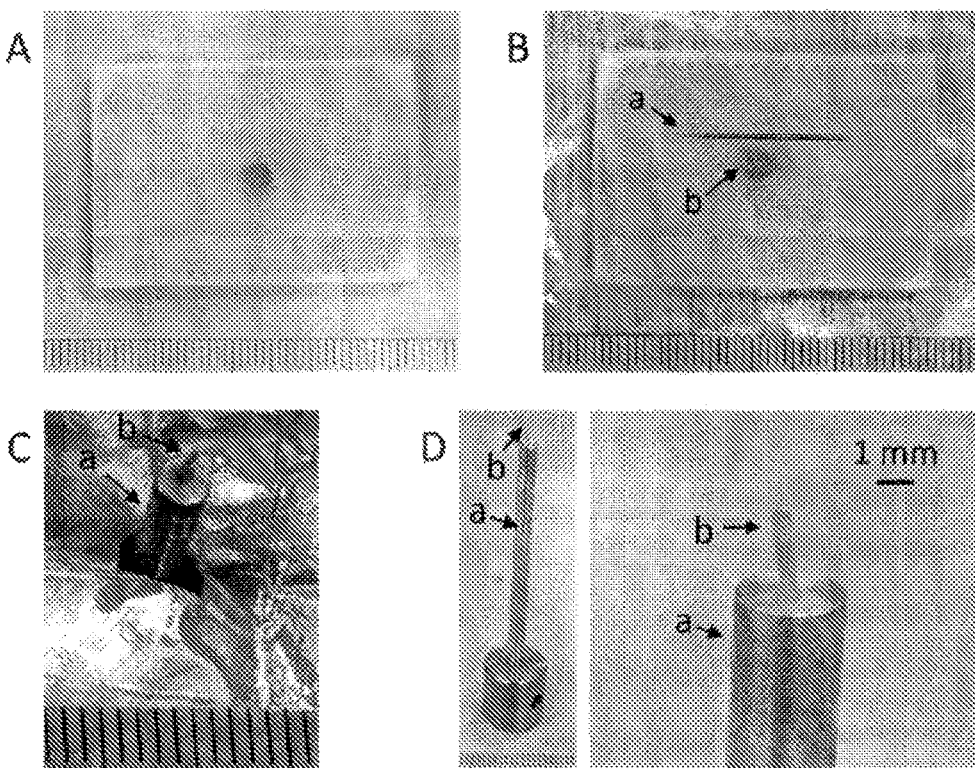
FIG. 1 shows a preparation example of a biological sample paraffin block applied with contrast imaging by paraffin. A: A paraffin block (an original sample) comprising a mouse kidney sample. A round object in the center of the block is a biological sample. B: Collection of an observation sample by a biopsy punch. A cylindrical biological sample with a diameter of 0.5 millimeter indicated by "a" was collected from a site of "b" of the paraffin block using the biopsy punch shown on the right of the biological sample. C: Melting and resolidifying of the paraffin contained in the biological sample. A state in which the cylindrical biological sample "b" with a diameter of 0.5 millimeter is erected on the upper surface of a metal bar "a" with a diameter of 3 millimeters is shown. A lower part of the metal bar across an aluminum foil is heated and thereafter cooled. D: A biological sample block applied with paraffin contrast imaging after preparation is shown. In each of a complete view (left) and enlargement of a sample part (right), a: the metal bar, b: the biological sample.

In an exemplary embodiment, the present disclosure relates to a method of obtaining an X-ray CT image of a biological sample, the method comprising a step of penetrating a contrast agent into the biological sample and solidifying the contrast agent to provide a contrast image of the biological sample, the contrast agent comprising wax and having a density of 0.95 g/cm$^3$ or less in its solidified state after penetration into the biological sample, and having a melting point of 40° C. to 80° C., a step of melting and resolidifying the solidified contrast agent, and a step of acquiring an X-ray CT image by irradiating the resolidified biological sample with an X ray having an energy of 4 to 12 keV, the shape of the biological sample being a shape with which a maximum optical path length of the X ray in the biological sample in the step of acquiring an X-ray CT image is 2 mm or less.

The method of the present disclosure can obtain a clear (for example, a voxel size is 5 μm or less, 4 μm or less, 3 μm or less, 2 μm or less, or 1 μm or less) high-quality X-ray CT image. The voxel size of the X-ray CT image indicates the size of a cubic pixel (a cube having the voxel size as one side). The voxel size can be calculated by dividing the size of a visual field of a CT image by the number of pixels included in the visual field.

As described herein, wax means a lipophilic compound that is solid at the normal temperature (20° C. to 30° C.) and has a melting point of 40° C. to 80° C. The wax may be either natural wax and synthetic wax. Examples of the wax include petroleum wax (natural wax), as examples, paraffin wax, microcrystalline wax, and petrolatum. Main components of these kinds of petroleum wax are saturated hydrocarbon, linear normal paraffin, branched-chain isoparaffin, and cyclic cycloparaffin. In an exemplary embodiment, the petroleum wax is solid paraffin. The solid paraffin means a mixture of alkanes with carbon numbers equal to or larger than 20. The petroleum wax may contain any one of the above waxes alone or a combination of the above waxes.

The contrast agent as described herein comprising the wax has a density of 0.95 g/cm$^3$ or less in its solidified state after penetration into the biological sample. In an exemplary embodiment, the density is a value at the normal temperature, for example, 20° C. to 30° C. or 25° C. The density of the contrast agent can be measured by a pycnometric method, a gravimetric method using Archimedes' principle, or the like.

The melting point of the contrast agent as described herein may be 40° C. to 80° C., for example, 45° C. or higher, 50° C. or higher, or 55° C. or higher and/or may be 80° C. or lower, 70° C. or lower, or 60° C. or lower. The melting point of the contrast agent can be measured by differential scanning calorimeter (DSC) or the like.

The contrast agent as described herein contains wax such as paraffin as a major component but may contain other components (for example, the contrast agent contains 50% or higher, 60% or higher, 70% or higher, 80% or higher, 90% or higher, 95% or higher, 98% or higher, 99% or higher, or 100% of wax such as paraffin with respect to the weight of the contrast agent).

As described herein, a "contrast agent" means an agent used to provide contrast to an image in an observation of a biological sample by X-ray CT (As described herein, the contrast agent is also described as a "low-density solidified contrast agent"). When the contrast agent as described herein is penetrated into a biological sample, the density of the solidified contrast agent is 0.95 g/cm$^3$ or less, which is lower than the density of water. Therefore, by penetrating the contrast agent into a biological sample (for example, a soft tissue, most of which has the same degree of density as the density of water), a density difference between the contrast agent and the biological sample can give contrast to an image in the observation by the X-ray CT. By penetrating the contrast agent as described herein into a cell and/or a tissue interstice of the biological sample, and solidifying the contrast agent, it is possible to suppress a change in a state of the biological sample (for example, movement of a soft and fragile biological sample during measurement) in the observation by the X-ray CT. Moreover, since X-ray absorption of the wax is in the middle between X-ray absorption of air and X-ray absorption of water, the wax does not cause a metal artifact (image noise that sometimes occurs when substances with significantly different X-ray transmittances are included in an imaging target) that occurs when heavy metal is used as the contrast agent. However, since wax is incompatible with water, the presence of moisture in a tissue hinders wax penetration. Therefore, in one aspect, sufficient dehydration with alcohol or acetone is performed before the contrast agent comprising the wax is penetrated and solidified.

As described herein, in the "step of penetrating a contrast agent into the biological sample and solidifying the contrast agent to provide a contrast image of the biological sample", the contrast agent as described herein is penetrated into the biological sample and solidified, whereby contrast is provided to an image in the subsequent observation of the biological sample by X-ray CT. Without limitation, the "step of penetrating a contrast agent into the biological sample and solidifying the contrast agent to provide a contrast image of the biological sample" can be performed by, for example, penetrating the contrast agent into a biological sample collected from a test subject, the contrast agent being liquefied by being heated to a temperature equal to or higher than a melting point of the contrast agent, and solidifying the contrast agent by cooling the contrast agent to the melting point or lower. By using a mold, the contrast agent can be solidified in any shape. When the mold is used, the solidified contrast agent does not need to be melted and resolidified because contrast imaging can be performed in a state in which a sample surface is smooth. However, the solidified contrast agent may be melted and resolidified to fix the biological sample to the sample table and to remove excess paraffin. The contrast agent can be more easily penetrated by using a contrast agent having low viscosity in a liquid state. Before the contrast agent is penetrated into the biological sample, one or more of the following steps may be performed: a step of chemically fixing the biological sample by immersing the biological sample in a fixing solution such as formalin or Bouin's solution, a step of dehydrating the fixed biological sample with alcohol such as ethanol or acetone, and a step of substituting the dehydrated sample with an intermediate agent such as xylene, propylene oxide, or chloroform in order to blend the dehydrated sample with the wax. As a fixation method, formalin fixation (using formaldehyde, paraformaldehyde, glutaraldehyde, or the like), alcohol fixation (using ethanol, methanol, acetone, chloroform, or the like), picric acid fixation (using Bouin's solution, alcohol Bouin's solution, or the like), and other fixation methods (HOPE, PAXgene) can be used. By performing these steps, it is possible to reduce tissue shrinkage, cracking, a change in cell structure, and the like involved in evaporation of moisture at the time when the contrast agent is penetrated into the biological sample and solidified. In addition to the steps described above, the step of penetrating a contrast agent into the biological sample and solidifying the contrast agent to provide a contrast image of the biological sample may further comprise, according to necessity, a step of degreasing the biological sample with acetone or the like and a step of decalcifying the biological sample with an acidic solution.

The step of melting and resolidifying the solidified contrast agent can be performed by, for example, heating the biological sample or a space around the biological sample and thereafter cooling the biological sample or the space. The melting of the solidified contrast agent may be performed by heating a heat-conductive portion in the case of an embodiment in which the heat-conductive portion (for example, a metallic sample table) is in contact with the biological sample. The heating of the heat-conductive portion (for example, the metallic sample table), if present, can be performed by, for example, immersing the heat-conductive portion in hot water bath of 40° C. or higher, 50° C. or higher, 60° C. or higher, 70° C. or higher, or 80° C. or higher for several minutes, for example, 1 to 30 minutes, 1 to 20 minutes, 1 to 5 minutes. The cooling can be performed by, for example, removing the heat-conductive portion from the hot water bath and resetting the heat-conductive portion to room temperature. By melting and resolidifying the solidified contrast agent, an excess contrast agent around the biological sample can be removed and the surface of the biological sample can be smoothened. This can prevent or reduce mixing of artifacts to an image due to sharp unevenness of the surface of the biological sample solidified by the contrast agent and/or prevent a contrast decrease in an X-ray absorption image that can occur when a large amount of the contrast agent is stuck to the biological sample. A heating time can be set as appropriate considering that there is a risk that even a necessary contrast agent leaks or the biological sample itself is altered if the heating time is too long. For example, the heating time can be set to the extent that the surface of the biological sample is not dried and/or the paraffin necessary for fixation is remained when the biological sample is directly fixed to the sample table. The heating time may be, for example, 30 seconds to 30 minutes, 1 minute to 10 minutes, 3 minutes to 8 minutes, or 5 minutes.

In an exemplary embodiment, the step of melting and resolidifying the contrast agent is performed in a state in which the biological sample is placed on the sample table. Consequently, an excess contrast agent around the biological sample is removed by melting and the surface of the biological sample can be smoothened. Further, since the biological sample is directly fixed to the sample table by the contrast agent by the resolidifying, noise that could occur in the image due to the use of another fixture (a tube, a film, or the like) can be reduced.

The step of acquiring an X-ray CT image by irradiating the resolidified biological sample with X rays having an energy of 4 to 12 keV can be performed by, for example, a usual method using an X-ray microscope. A type of the X-ray microscope is not limited. However, for example, nano3DX (Rigaku Corporation) can be used.

An X-ray tube and synchrotron radiation are known as an X-ray source. The X-ray tube is a device that generates an X ray by accelerating and focusing thermal electrons emitted from a cathode (a filament) with a potential difference between the cathode and an anode and causing the thermal electrons to collide with the anode (a target). The X ray generated by the X-ray tube includes a continuous X ray due to bremsstrahlung of the accelerated electrons and a characteristic X ray (indicating a bright line spectrum) involved in excitation and transition of extranuclear electrons of atoms constituting the target.

In an exemplary embodiment, the X ray as described herein includes a characteristic X ray deriving from targets such as Ti, Cr, Cu, and Ga. Using Ti, Cr, Cu, Ga, and the like as target materials enables use of a sensitive low-energy characteristic X ray. In an exemplary embodiment, the energy of the X ray is 5 to 9 keV or 5.41 to 8.04 keV.

The synchrotron radiation is an X ray generated in a synchrotron (a type of a circular accelerator) when the orbit of an electron beam accelerated to nearly the speed of light is changed by a magnet or the like. Since the diameter of the synchrotron reaches, for example, several tens of meters or more, a large facility is usually required to use the synchrotron radiation. In an exemplary embodiment, the X ray as described herein is not synchrotron radiation. In this embodiment, the method as described herein does not require a large facility.

In an exemplary embodiment, the method as described herein does not use contrast agents (for example, osmium, iodine, and barium) other than the contrast agent explained above. In this embodiment, a contrast imaging step by the other contrast agents is not necessary. Metal artifacts and image alterations caused by the use of other contrast agents can be reduced (for example, since osmium tetroxide used as a contrast agent chemically reacts with and binds to a biological component having a double bond, unsaturated fatty acid or the like containing many double bonds is sometimes emphasized in an X-ray CT image).

In this specification, a type of the biological sample is not limited but may be a cell, a tissue, an organ, or an organ system of a mammal comprising a human, a bird, a reptile, an amphibian, an insect, fish, a benthic animal, a plant, or the like. Examples of the organ or the organ system include a kidney, a liver, a heart, pancreas, an intestinal tract, a stomach, a lung, a brain and a nerve, a bone and a muscle, a blood vessel, a sensory organ, a reproductive organ, and an organoid as well as a bioabsorbable polymer scaffold material that can be used for tissue and organ regeneration.

To obtain an X-ray CT image with a spatial resolution of approximately several tens of micrometers or less, 10% or more of an irradiation X ray needs to be transmitted through a sample. An X-ray attenuation length of water having an X-ray absorption coefficient equal to that of a biological substance is approximately 1 mm when X-ray energy is 8 keV, which means that an X ray attenuates by almost one order of magnitude when the X ray passes through a 2 mm thick biological sample. Therefore, when the X-ray energy is 8 keV, if the biological sample is processed into a biological sample with a maximum optical path length of the X ray of 2 mm or less (for example, a shape, whose maximum width in the X-ray transmission direction is 2 mm or less, such as a column with a diameter of approximately 2 mm or less), the biological sample can be observed with an X-ray transmittance of 10% or higher. Examples of a biological sample with a maximum optical path length of an X ray of 2 mm or less include a shape with a diameter of 2 mm or less or 1 mm or less or a maximum width of 2 mm or 1 mm or less (for example, a prismatic shape). As described herein, a shape with a maximum width of 2 mm may be a prismatic shape, for example, a triangular prism, a square prism (for example, a rectangular parallelepiped), a pentagonal prism, or a hexagonal prism. As described herein, a columnar or prismatic shape includes a substantially columnar or substantially prismatic shape. In one aspect, the biological sample solidified by the contrast agent as described herein is a column because of compatibility with CT reconstruction.

As described herein, the "optical path length" of the X ray in the biological sample in the step of acquiring an X-ray CT image means, assuming that an X-ray refractive index of the biological sample is 1, the length of a path on which the X ray passes through the sample. In the step of acquiring an X-ray CT image, a large number of X-ray projection images are obtained from different directions by rotating the sample. A maximum optical path length of the X ray in those projection images is defined as "the maximum optical path length of the X ray in the biological sample in the step of acquiring an X-ray CT image". The maximum optical path length of the X ray is obtained by measuring a maximum length of the biological sample in a direction perpendicular to a sample rotation axis at the X-ray CT data imaging time. For example, one X-ray projection image can be taken in a direction in which a side having the maximum length is perpendicular to an X-ray irradiation direction and the maximum length of the biological sample in the direction perpendicular to the sample rotation axis can be measured using image analysis software such as ImageJ. More accurately, the maximum length of the biological sample in the direction perpendicular to the sample rotation axis can be measured from a projected image (Sinogram) in the sample rotation axis direction created by ImageJ or the like from the X-ray CT projection image data.

As described herein, the maximum width of the shape means a maximum length of the shape in the direction perpendicular to the sample rotation axis at the X-ray CT data imaging time. In an exemplary aspect, the lower limit of the diameter or the maximum width of the biological sample is not limited but is 0.1 mm or more, 0.3 mm or more, or 0.5 mm or more because of a processing technology problem.

The height of the column or the shape as described herein (the length in the sample rotation axis direction at the X-ray CT data imaging time) is not limited.

In an exemplary embodiment, the method of obtaining an X-ray CT image as described herein further comprises, before the step of penetrating a contrast agent into the biological sample and solidifying the contrast agent to provide a contrast image of the biological sample, a step of cutting the biological sample into a shape in which the maximum optical path length of the X ray in the biological sample in the step of acquiring an X-ray CT image is 2 mm or less. The contrast agent is penetrated into the biological sample obtained by the step and solidified to provide a contrast image of the biological sample (in this case, a mold may be used to perform solidification to provide a contrast image of the biological sample such that the biological sample after the solidification has said shape). In another embodiment, the method of obtaining an X-ray CT image as described herein comprises, before the step of melting and resolidifying the solidified contrast agent after the step of penetrating a contrast agent into the biological sample and solidifying the contrast agent to provide a contrast image of the biological sample, a step of cutting the solidified biological sample into a shape in which the maximum optical path length of the X ray in the biological sample is 2 mm or less in the X-ray CT image acquisition step. The step of cutting the biological sample can be performed using a cylindrical pipe, for example, a seamless cylindrical pipe having a diameter of 2 mm or less and having a sharp cutting edge, for example, a biopsy punch. The step of cutting the biological sample may be performed with the cylindrical pipe heated to a temperature higher than the melting point of the contrast agent. Consequently, since it is possible to collect the biological sample while melting the contrast agent, the biological sample can be collected in a state in which cracks less easily occurs and the surface of the biological sample is smooth.

In an exemplary embodiment, the method as described herein further comprises a step of adding a marker to the biological sample, and in the step of acquiring an X-ray CT image, the X-ray CT image is corrected by moving slices of the X-ray CT image according to movement of a projected marker image obtained from the X-ray projection image of the marker. An observation by the X-ray CT sometimes lasts for several hours to 48 hours or several hours to 24 hours. Image quality is sometimes deteriorated by drift (movement of an observation sample in micrometer units during imaging). In this case, a clearer image can be obtained by performing the correction explained above.

As described herein, the marker means a mark used for the drift correction explained above. As the marker, a material having a sufficiently higher density than the biological sample, for example, diamond, graphite, silicon, titanium, and aluminum can be used.

The step of adding a marker to the biological sample can be performed by, for example, dispersing the marker in the contrast agent by resolidifying the wax as described herein comprising the marker (for example, when diamond is used as the marker, the marker can be obtained by cutting a solidified wax with a diamond wire saw) after heat-melting the wax comprising the marker together with the biological sample solidified by the contrast agent as described herein. Marker concentration in the contrast agent is desirably a degree for giving a situation in which drift correction is possible (that is, a situation in which one or more single-particle markers are present in desirable positions in an X-ray obtained image and are distinguishable from other markers). In an exemplary aspect, the marker is added in a position close to the sample rotation axis on the biological sample surface. When the marker is added in a position far from the axis, the marker sometimes deviates from a visual field according to sample rotation during X-ray imaging. In this case, the drift correction is difficult.

The drift correction can be performed by correcting the X-ray CT image by moving slices of the X-ray projection image according to the movement of projected marker image obtained from the X-ray projection image of the biological sample to which the marker is added. The correction can be performed, for example, as follows according to the description of the examples in this application specification. That is, the X-ray projection image of the biological sample to which the marker is added (a large number of continuous image data obtained by sequentially systematically changing a sample direction while rotating the sample) is read by software such as the program ImageJ and a projected image (Linogram) in a direction of a track of the marker perpendicular to the sample rotation axis is created. Subsequently, the projected image is further processed to extract a single track. The position of this line converted into a numerical value is a drift amount in the sample rotation axis direction. Subsequently, the X-ray CT image can be corrected by moving in parallel the slices of the X-ray projection image of the biological sample up and down to cancel the drift amount.

Figure 8:
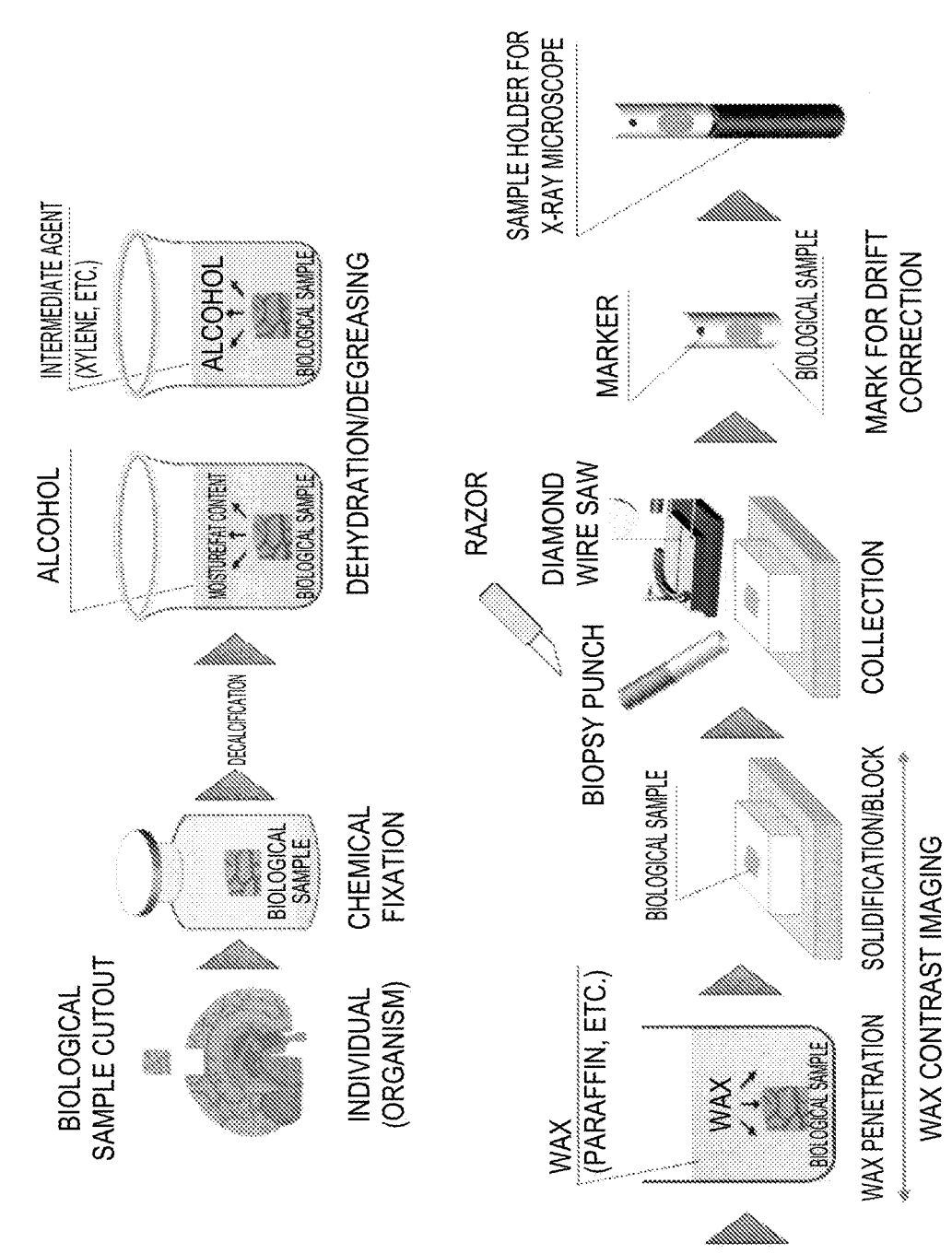
FIG. 8 shows an embodiment of a method of obtaining an X-ray CT image of a biological sample of the present disclosure.

An exemplary embodiment of the step of penetrating a contrast agent into the biological sample and solidifying the contrast agent to provide a contrast image of the biological sample in the method of obtaining an X-ray CT image of a biological sample of the present disclosure is shown in FIG. 8. First, a sample is cut out from an organism. Subsequently, chemical fixation is performed to protect the biological sample from degradation due to autolysis or decay. The chemical fixation can be any one of formalin fixation (using formaldehyde, paraformaldehyde, glutaraldehyde, or the like), alcohol fixation (using ethanol, methanol, acetone, chloroform, or the like), picric acid fixation (using Bouin's solution, alcohol Bouin's solution, or the like), other fixation methods (HOPE, PAXgene), and the like. Subsequently, a dehydration process for removing moisture (in an exemplary aspect, completely removing moisture) from a biological tissue by replacing moisture in the tissue with alcohol or the like is performed. The dehydration process can be performed using ethanol series, acetone series, or other solutions. After the dehydration process, an intermediate agent treatment process, which is treatment for replacing alcohol or the like in the biological tissue with an intermediate agent, is performed. The intermediate agent treatment process can be performed using xylene, propylene oxide, chloroform, and the like. Subsequently, a contrast agent penetration process is performed. In the contrast agent penetration process, a contrast agent comprising wax and having a density of 0.95 g/cm$^3$ or less in its solidified state after penetration into biological sample, and having a melting point of 40° C. to 80° C. is penetrated into the biological sample. Subsequently, an excess contrast agent around the biological sample may be removed using a diamond wire saw, a razor, or the like. A part of a larger biological sample may be collected by a seamless cylindrical pipe having a sharp cutting edge of 2 mm or less in diameter such as a biopsy punch (the cylindrical pipe may be heated in the collection process to a temperature higher than the melting point of the contrast agent). For the purpose of drift correction, a pointing marker, for example, diamond, graphite, silicon, titanium, and aluminum may be given to the biological sample. In the step of adding the marker to the biological sample, for example, when diamond is used, the marker can be obtained by cutting a solidified contrast agent with a diamond wire saw. Subsequently, melting and resolidifying treatment may be performed. By this removing the excess contrast agent around the biological sample, it is possible to finally reduce the maximum optical path length of the X ray to 2 mm or less, smooth the sample surface, and fix an X-ray microscope to a sample holder.

In an exemplary embodiment, the present disclosure relates to a method of analyzing a biological sample, comprising:

a step of penetrating a contrast agent into a biological sample and solidifying the contrast agent to provide a contrast image of the biological sample, the contrast agent comprising wax and having a density of 0.95 g/cm$^3$ or less in its solidified state after penetration into the biological sample, and having a melting point of 40° C. to 80° C.;

a step of melting and resolidifying the solidified contrast agent;

a step of acquiring an X-ray CT image by irradiating the resolidified biological sample with an X ray having an energy of 4 to 12 keV, the shape of the biological sample being a shape with which a maximum optical path length of the X ray in the biological sample in the step of acquiring an X-ray CT image is 2 mm or less;

a step of specifying a site to be further observed by an optical microscope and/or an electron microscope based on the acquired X-ray CT image and cutting and exposing the site;

a step of observing the site with the optical microscope and/or the electron microscope; and a step of combining the X-ray CT image and results of the observation by the optical microscope and/or the electron microscope to analyze the biological sample.

In this analysis method, the step of penetrating a contrast agent into the biological sample and solidifying the contrast agent, the step of melting and resolidifying the solidified contrast agent, and the step of acquiring an X-ray CT image are respectively as explained herein about the steps of the method of obtaining an X-ray CT image.

Figure 4:
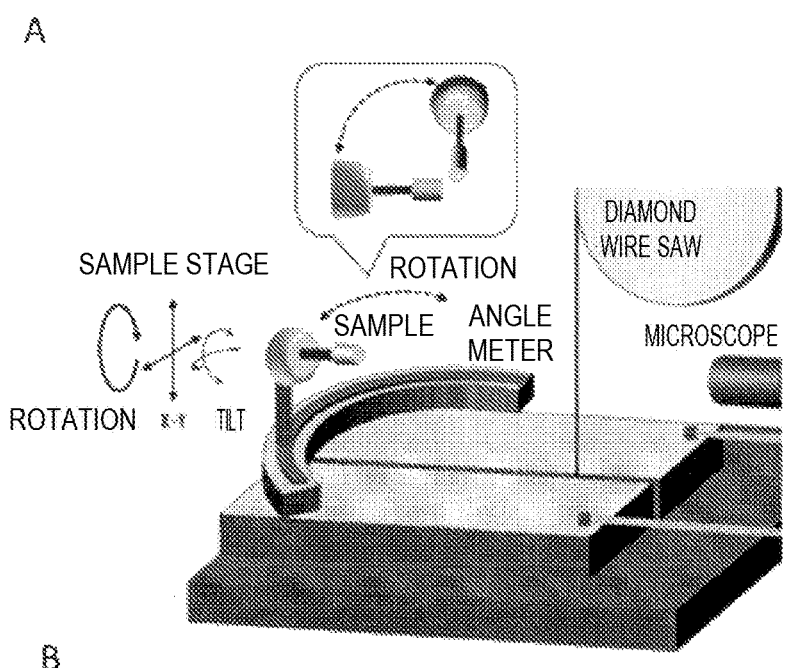
FIG. 4 shows a device in which a sample attachment is attached to a commercially available diamond wire saw. A: A schematic diagram of the device. B: A CT image of Epon resin-embedded osmium (Os) contrast imaging. Images of before excess resin trimming (upper) and after excess resin trimming (lower) by the diamond wire saw were compared. Contrast was improved a little by the trimming. C: Cutting of a biological sample in a paraffin block. A long cylindrical biological sample was cut into halves by the diamond wire saw. An object indicated by an arrow is one of halved pieces of the biological sample.
Figure 4:
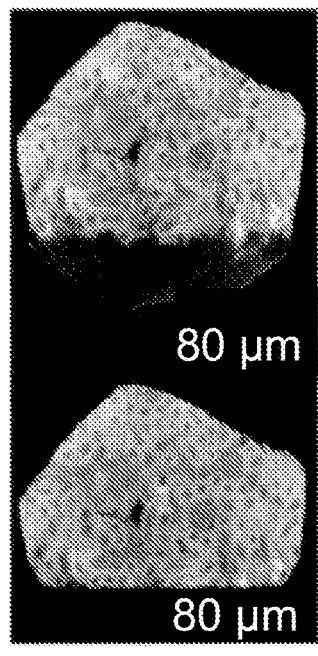
Figure 4:
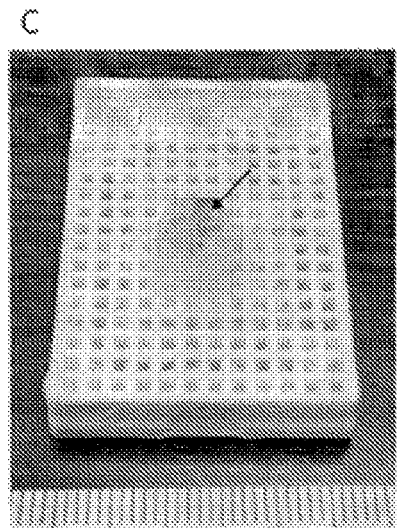

The step of specifying a site to be further observed by an optical microscope and/or an electron microscope based on the acquired X-ray CT image and cutting and exposing the site can be performed, for example, as explained below. First, as shown in FIG. 1D, the step of acquiring an X-ray CT image is performed in a state in which the contrast agent is melted and resolidified on the sample table and the sample is fixed on the sample table by the contrast agent. Subsequently, in a commercially available cutting device (for example, a diamond wire saw of Musashino Denshi, Inc., or WELL Diamond Wire Saws, Inc.), a commercially available unit is removed according to necessity, an angle meter is installed anew as shown in FIG. 4, and the sample table to which the biological sample is fixed is transferred to a sample stage unit of an X-ray microscope attached to the angle meter. The sample stage unit is enabled to rotate and move on an X-Y axis and desirably provided with a tilt mechanism (a mechanism for adjusting a direction shown in FIG. 4A) and the angle meter is enabled to move in a range of 90° or more to make it possible to cut the biological sample according to a purpose. Here, a mark (fiducial) for determining an angle can be provided in the sample table, and the sample table can be installed in the sample stage unit according to the fiducial. The cutting can be performed based on information (a numerical value) obtained by imaging with X-ray CT while being checked by a microscope equipped with a cutting machine.

When optical microscopic observation is performed after the cutting by the diamond wire saw, the biological sample is removed from the sample table, penetrated with a paraffin block having a standard compatible with a microtome and solidified, and sectioned by the microtome using a cutting surface by the diamond wire saw as a mark, and an observation sample for an optical microscope is prepared according to a usual method. On the other hand, when electron microscopic observation is performed after the cutting by the diamond wire saw, the biological sample is removed from the sample table, deparaffinized, embedded in an Epon resin block having a standard compatible with the microtome, and ultrathin section by the microtome is performed using a cutting surface by the diamond wire saw as a mark, and an observation sample for an electron microscope is prepared according to the usual method. The surface of the sample may be smoothed by ion milling, a cross-section polisher (TM), or the like according to necessity. When it is found as a result of the X-ray CT observation that the cutting by the diamond wire saw is unnecessary, the method can omit the cutting, and proceed to an observation by an optical microscope or an electron microscope.

In an exemplary embodiment, the "step of penetrating, into the biological sample, a contrast agent, solidifying the contrast agent, and contrast-imaging the biological sample" can be performed by the same procedure as the step of paraffin embedding.

Since the analysis method can observe the biological sample by combining the X-ray CT image and the optical microscope and/or the electron microscope, more detailed information can be obtained than when an observation is performed by any one of the X-ray CT image, the optical microscope, and the electron microscope alone. First, unlike the optical microscope and the electron microscope, in the X-ray CT, since an observation in three dimensions is possible and a subject can be examined nondestructively, the biological sample can be observed in a form closer to its original state. On the other hand, since the X-ray CT is inferior in spatial resolution compared with the optical microscope and the electron microscope in general, by specifying a site to be observed based on an X-ray CT image and performing an observation by the optical microscope or the electron microscope for the site, the site can be observed more in detail.

The method of obtaining an X-ray CT image of a biological sample and the method of analyzing biological sample as described herein can be used for a diagnosis of a disease or a disorder or support therefor, and for cell and/or tissue research purposes.

In an exemplary embodiment, the disclosure relates to a contrast agent for X-ray CT of a biological sample, the contrast agent comprising wax as described herein and having a density of 0.95 g/cm$^3$ or less in a solidified state after penetration into the biological sample, and having a melting point of 40° C. to 80° C. Details of the contrast agent are as described herein about the method of obtaining an X-ray CT image of a biological sample.

EXAMPLES

Example 1: Preparation of a Sample

The temperature of a biological sample solidified in a paraffin block (approximately 35×25×5 mm) to provide a contrast image of the biological sample (a mouse kidney section chemically fixed by 4% paraformaldehyde for 16 hours at room temperature, dehydrated by ethanol, and thereafter penetrated with paraffin (a paraffin stick CT-PARA-ST manufactured by Genostaff Co., Ltd.) having a melting point of 56 to 58° C. and a density of approximately 0.90 g/cm$^3$ and solidified; FIG. 1A) was set higher than the melting point of the paraffin to melt the paraffin. Specifically, first, a part of a mouse kidney in the paraffin block was cut into a 0.5 mm diameter cylindrical shape using a dermatological biopsy punch (KAI Industries Co., Ltd., a disposable biopsy punch 0.5 mm, BP-A05F) (FIGS. 1A and 1B). This cylindrical sample was placed on the upper surface of a 3 mm diameter cylindrical metal bar, which is a standard sample attachment jig of an X-ray microscope (Rigaku Corporation, nano3DX) (FIG. 1C). In this state, excess paraffin around the sample was melted and drained out by heating a lower part of the metal bar with hot water bath (for a heating time of approximately 5 minutes at a water temperature of approximately 90° C.). At the same time, a disposable pipette tip (Molecular Bioproducts, 0.1-10 μl, cat #103) and hair were used to adjust the orientation of the sample such that a long axis of the sample and a long axis of the metal bar became approximately parallel. Thereafter, when the hot water bath was removed, the paraffin in the sample was cooled at room temperature to be solidified while smoothness of the surface was maintained, and the sample was fixed in a nearly naked state, standing on the metal bar (FIG. 1D). The biological sample applied with contrast imaging by the paraffin was prepared by the method explained above.

Example 2: Adding a Marker to the Biological Sample

Figure 2:
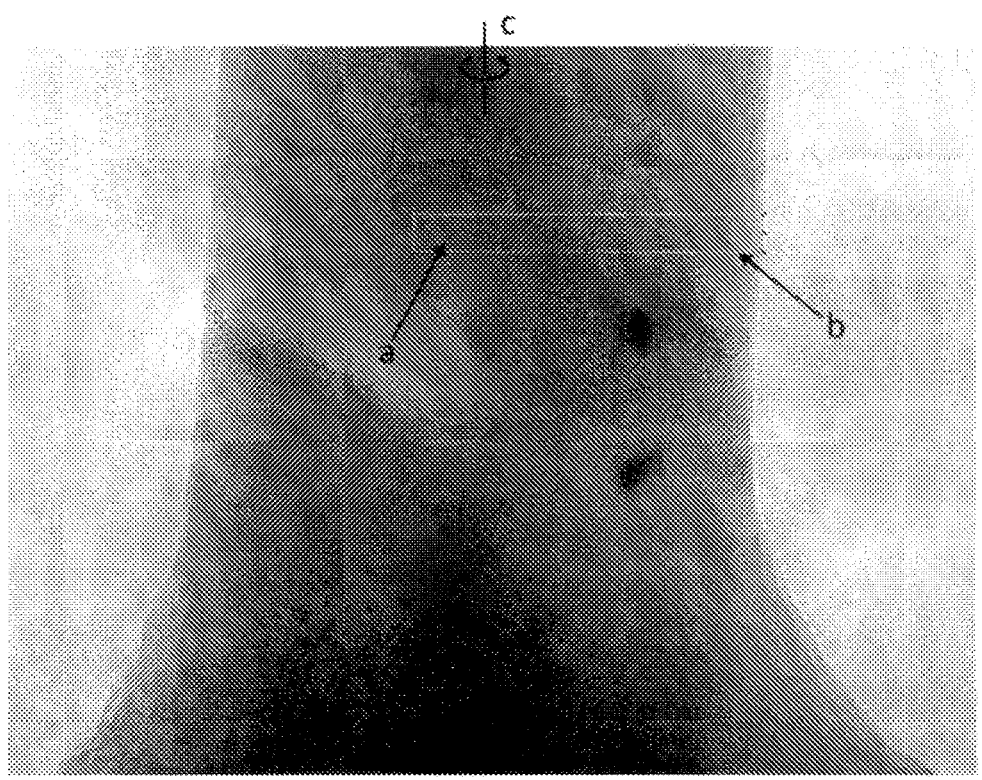
FIG. 2 shows one X-ray projection image of a biological sample applied with contrast imaging by paraffin. A single particle (seen as a black dot) with a diameter of 2 to 3 microns actually used as a position marker is shown with "a". A region "b" surrounded by a frame is a marker presence range during imaging. Since this marker particle is present near a sample rotation axis "c", the marker particle does not deviate from a visual field according to sample rotation during the imaging.

The following step was added to the preparation method for the biological sample applied with the contrast imaging by the paraffin described in Example 1. Diamond wire saw chips (presumably diamond particles) were used as a marker. Specifically, when a part of the sample block was placed on the 3 mm diameter metal bar and the hot water bath was performed in Example 1, approximately 1 mg of a paraffin piece comprising the marker (a black portion of a cutting surface of the paraffin block cut by a diamond wire saw (Musashino Denshi, Inc.) and shaved off by a knife) was additionally placed on the metal bar and the marker was dispersed in the paraffin by thermal melting. Consequently, the marker was successfully added to a position close to the sample rotation axis (FIG. 2). If the marker is added to a position far from the sample rotation axis, the marker sometimes deviates from a visual field according to sample rotation during imaging. In this case, drift correction is difficult.

Example 3: Drift Correction

Drift correction was performed by processing X-ray projection images of the biological sample applied with the contrast imaging by the paraffin (approximately several hundred or several thousand continuous image data imaged by sequentially systematically changing a sample direction with rotation around the sample rotation axis) according to the following procedure. An image shown in FIG. 2 in Example 2 is one of the X-ray projection images explained above.

Figure 3:
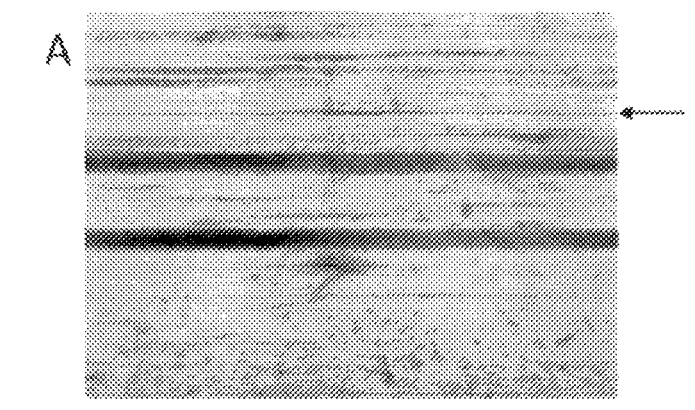
FIG. 3 shows an example of drift correction. A: A projected image of a track of an entire marker at the time when a series of X-ray projection images are read. B: A projected image of a track of a single marker particle. One line (an arrow in FIG. 3A) connected from an end to an end in an entire projected image is extracted. Particularly large displacement is seen in two places indicated by *. C: Comparison of CT images before (left) and after (right) the drift correction.
Figure 3:
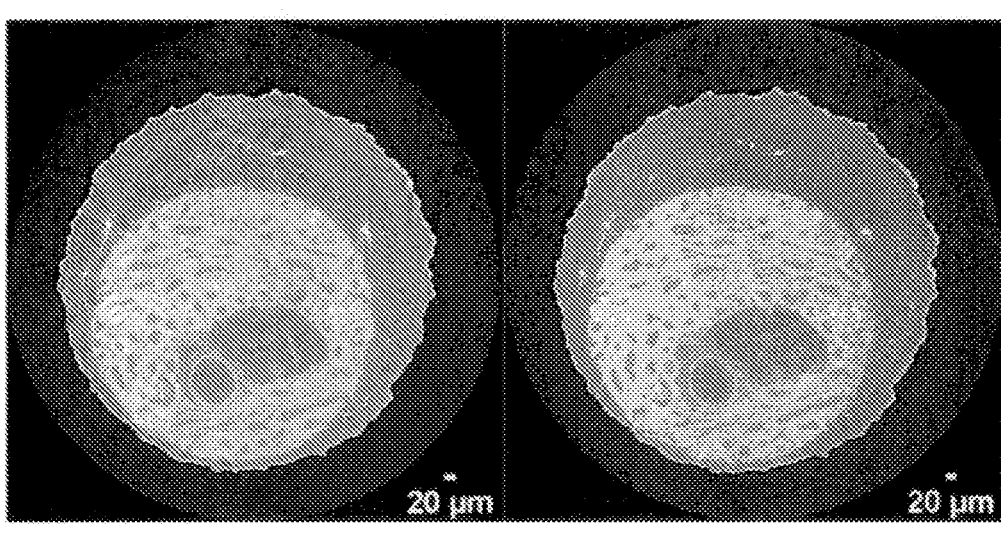

1) A series of X-ray projection images were read by the program ImageJ (free software) to create a projected image (Linogram) of a track of a marker in a direction perpendicular to the sample rotation axis (FIG. 3A).

2) The projected image was further processed to extract one track (FIG. 3B). Here, one line connected from an end to an end present in positions of approximately ¼ from the top of the image shown in FIG. 3A was used (an arrow in FIG. 3A). The position of this line converted into a numerical value is an up-down drift amount. Particularly large displacement was seen in two places indicated by star marks in FIG. 3B.

3) Slices of the projection image was moved in parallel up and down to cancel the drift amount.

When CT images before and after the drift correction are compared, radial noise and the like appearing around an object were markedly reduced (FIG. 3C).

Example 4: Cutting Out by a Cutting Machine of a Part of Interest Observed by an X-Ray Microscopic Observation The standard jig of the commercially available diamond wire saw (Musashino Denshi, Inc.) was removed and an angle meter was installed anew as shown in FIG. 4. A sample stage unit of an X-ray microscope was attached to the angle meter.

1) For an Epon resin-embedded sample of an Os contrast-imaged mouse kidney (a sample shown in FIG. 5A in Example 5), resin was trimmed using a diamond wire saw. As a result, the contrast of a CT image was slightly improved (FIG. 4B).

2) For a sample (a mouse kidney) applied with contrast imaging by paraffin, a diamond wire saw was used to cut an excessively long cylindrical sample in a paraffin block into appropriate lengths (FIG. 4C). There is a high risk of damaging the sample if the sample is cut into pieces by a razor.

Example 5: Comparison with the Related Art

A renal corpuscle of a mouse kidney was used as a sample to compare an observation example of the related art stained with osmium tetroxide and an exemplary embodiment of the present disclosure in which paraffin was used as a low-density solidified contrast agent. The observation was performed using an X-ray microscope nano3DX (Rigaku Corporation) (a CCD detector) and an 8.0 keV characteristic X ray from a Cu-target. Using a rotating anode high-brightness X ray adopted in nano3DX is effective to reduce a total exposure time required for data recording (for example, to reduce the time to approximately 24 hours or less). Reducing the influence of light source drift with a proximity imaging method adopted in nano3DX is effective to increase spatial resolution (for example, to perform the observation with submicron spatial resolution).

In an observation example of the related art, mouse kidney sections were chemically fixed by 2.4% glutaraldehyde at 4° C. for 2 hours, stained with 1% osmium tetroxide at 4° C. overnight, dehydrated with acetone, and thereafter embedded in Epon resin to form a resin block. A tip portion of the resin block comprising the kidney sections was substantially isotropically trimmed to 0.7-0.8 mm and the trimmed portion was observed with an X-ray microscope (FIG. 4B, top). A sample was attached to an X-ray microscope nano3DX (Rigaku Corporation) (a CCD detector) and X-ray projection image data was obtained under conditions of Cu-target (40 kV/30 mA), L0270-bin2-XD5 (0.53 μm/voxel), and Step scan (1600 exposures of 30 s each) (time required: 13.8 hours). The projection image data was processed by a general noise reduction filter (median 1 and Gaussian 1) and thereafter CT reconstruction was performed by software based on a general FBP algorithm.

Sample preparation in the case in which paraffin was used as a low-density solidified contrast agent was performed according to Example 1. A sample was attached to an X-ray microscope nano3DX (Rigaku Corporation) (a CCD detector) and X-ray projection image data was obtained under conditions of Cu-target (40 kV/30 mA), L0270-bin2-XD2 (0.54 μm/voxel), Step scan (1,700 exposures of 40 s each) (time required: 19.4 hours). After the projection image data was processed by a general noise reduction filter (median 1 and Gaussian 1), CT reconstruction was performed by nano3DX standard software based on a general FBP algorithm.

Figure 5:
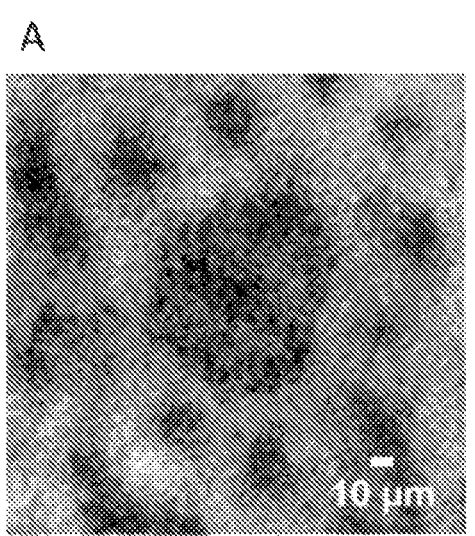
FIG. 5 shows comparison of X-ray CT images. A: A result of Epon resin-embedded osmium (Os) contrast imaging. A circular structure seen in a photograph center is a cross section of a spherical renal corpuscle (having a diameter of approximately 80 microns). B: A result of paraffin contrast imaging. A circular structure seen in a photograph center is a cross section of a spherical renal corpuscle (having a diameter of approximately 80 microns).
Figure 5:
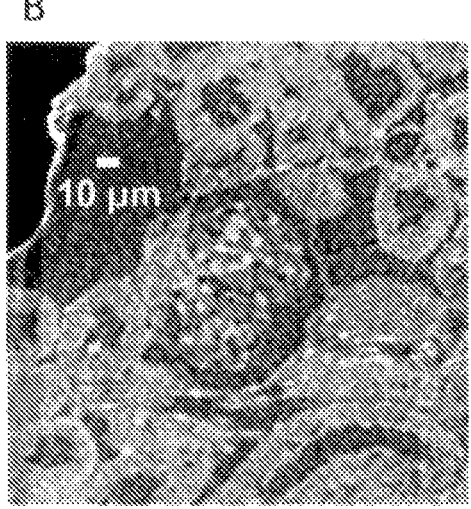

Results are shown in FIG. 5. FIG. 5A shows a result of Epon resin-embedded Os contrast imaging. Since X-ray absorption by the sample is large, sufficient contrast was not obtained by exposure for 13.8 hours and substantial spatial resolution was approximately 10 μm. FIG. 5B shows a result of contrast imaging by paraffin. Sufficient contrast was successfully obtained after exposure for 19.4 hours and substantial spatial resolution was approximately 0.9 μm. A microstructure inside the renal corpuscle was also successfully discriminated. FIG. 5B shows a result in the case in which drift correction by a marker was performed. The spatial resolution was measured from a luminance value line profile of a substance boundary in a CT slice image according to, for example, a method described in the following literature: Kunishima et al. Plant Methods (2020) 16:7.

Example 6: Collection of a Sample Using a Heat-Treated Instrument

A dermatological biopsy punch (KAI Industries Co., Ltd. a disposable biopsy punch 1.0 mm, BPP-10F) immersed in 90° C. hot water for 20 seconds and heat-treated and the biopsy punch not heat-treated were used to collect paraffin from a paraffin block (McCormick Scientific Institute, PARAPLASTPLUS 502004, melting point 56° C.). Thereafter, the collected sample was imaged close-up to obtain an optical photograph and observed by an optical microscope (a zoom stereomicroscope (with LED illumination) CP745, As One Corporation).

Figure 6:
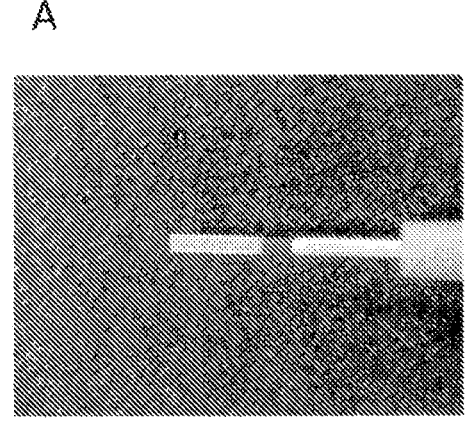
FIG. 6 shows a surface observation result of paraffin collected from a paraffin block using a heat-treated biopsy punch and a not heat-treated biopsy punch (FIG. 6A: an optical photograph in the case in which the paraffin was collected using the heat-treated biopsy punch.
Figure 6:
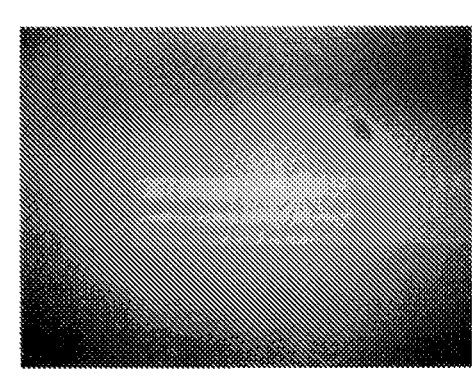
Figure 6:
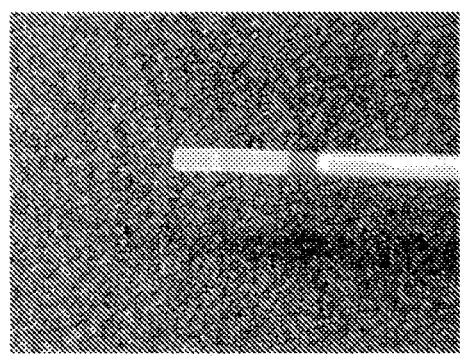
Figure 6:
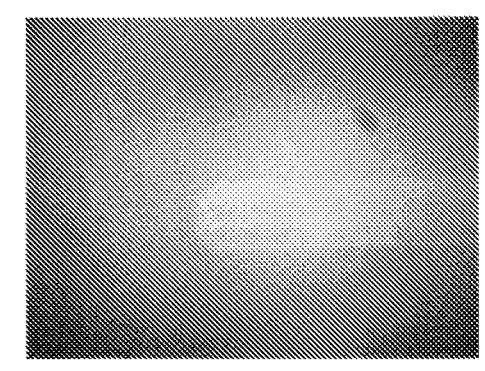

Results are shown in FIG. 6 (FIG. 6A: an optical photograph in the case in which paraffin was collected using the heat-treated biopsy punch. FIG. 6B: an optical microscope photograph in the case in which paraffin was collected using the heat-treated biopsy punch. FIG. 6C: an optical photograph in the case in which paraffin was collected using the not heat-treated biopsy punch. FIG. 6D: an optical microscope photograph in the case in which paraffin was collected using the not heat-treated biopsy punch). As shown in FIG. 6, compared with when the heat treatment was performed, a crack occurred in the center of the paraffin and a contour of the paraffin was unclear when the heat treatment was not performed. This indicates that, since the biological sample can be collected while dissolving the contrast agent by using the heat-treated biopsy punch, the biological sample can be collected in a state in which a crack less easily occurs and the surface is smooth.

Example 7: Test Using a Polyimide Tube

Since an X-ray attenuation length of polyimide at 8 keV (mm) is 1.2 and is a value close to 1.0, which is an X-ray attenuation length of water (considered to be substantially equivalent to an organism) under the same conditions, it was considered that a contrast imaging effect of wax could be evaluated using polyimide instead of the biological sample. Therefore, the contrast imaging effect of the wax was evaluated by the following method.

Figure 7:
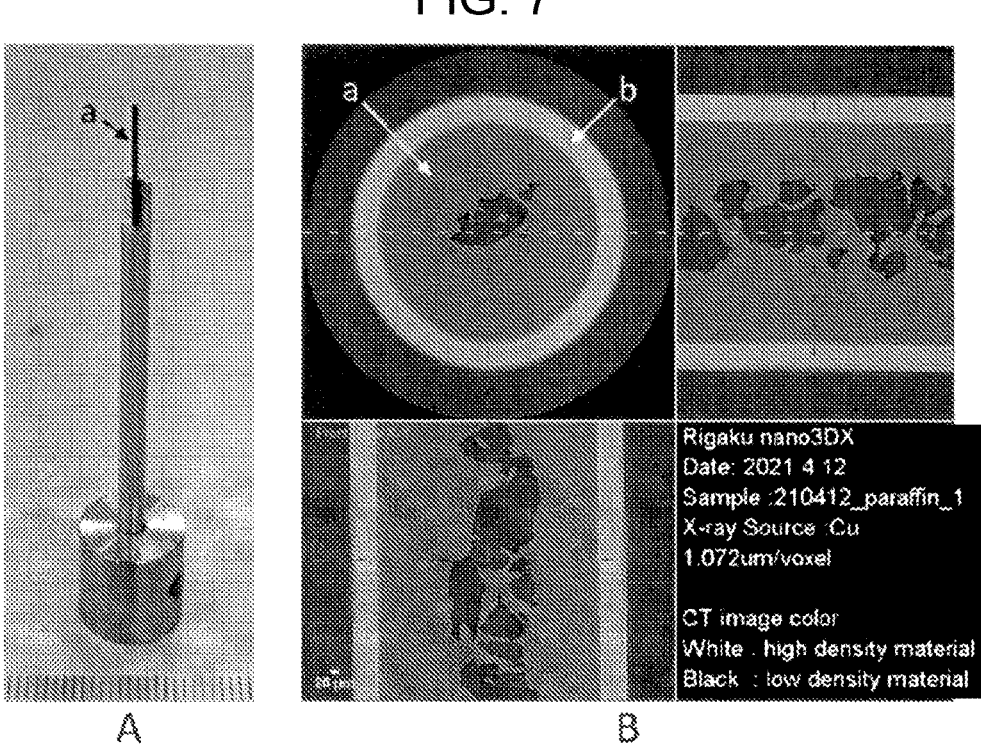
FIG. 7 shows an evaluation example of a contrast imaging effect by wax. A: A measurement sample. "a" is a polyimide tube filled with wax (paraffin). B: Orthogonal CT slices from three directions. "a" is a wax region and "b" is a polyimide region. The contrast imaging effect of the wax was evaluated by measuring an SN ratio between both the regions. A portion seen black near a tube center is a hollow formed in wax solidification.

Waxes described in Table 1, which were thermally melted by hot water bath at approximately 90° C., were sucked into a polyimide tube with an inner diameter of 0.5 mm (a polyimide tube PIT-S manufactured by Furukawa Electric Co., Ltd. (an inner diameter 0.50 mm, thickness 0.06 mm)) by capillary action by approximately length of 5 to 10 mm and cooled at room temperature to be solidified. The polyimide tube filled with the waxes was bonded to the tip portion of a sample table for an X-ray microscope by an adhesive (Aron Alpha by TOAGOSEI CO., LTD.) (FIG. 7A). At this time, a sample rotation axis and a long axis of the polyimide tube were substantially aligned (adjusted not to protrude from a visual field of the X-ray microscope in a direction perpendicular to the sample rotation axis). The sample table was attached to an X-ray microscope nano3DX (Rigaku Corporation) (a CCD detector) and X-ray projection image data was obtained under conditions of Cu-target (40 kV/30 mA), L0270-bin4-XD2 (1.07 μm/voxel), and Step scan (700 exposures of 10 s each) (time required: 2.2 hours). After the projection image data was processed by a noise reduction filter (median 1 and Gaussian 1), CT recon- struction was performed by nano3DX standard software based on a general FBP algorithm. Since orthogonal CT slices from three directions were output as a tiff-format report file, this report was input to free software ImageJ and an image analysis was performed (FIG. 7B). A 15×15 pixel square portion was optionally taken in each of a wax region and a polyimide region and an average luminance value and a standard deviation in the portion were measured. A value obtained by dividing the difference between average lumi- nance values of the two regions by a standard deviation thereof (a square root of (a sum of variances of the two regions)) was defined as an SN ratio (a reference literature: KUNISHIMA N. et al., PLANT METHODS 16:7 (2020)). This measurement was performed in five places and an average value and a 95% confidence interval thereof were calculated (Table 1). The measurement places were selected from the three directions in the report not to be biased. Results of performing similar measurement for polyethylene glycol (obtained by drying 50% PEG3350 aqueous solution manufactured by Hampton Research Corp.) as a negative example and for the mouse kidney sample described in Example 5B as an example of an actual biological sample are additionally shown. In the mouse kidney sample, an SN ratio between wax (paraffin) and a biological tissue (tubules) was measured. The SN ratio was approximately 18 for all five kinds of commercially available paraffin, approximately 2.5 for polyethylene glycol, and approximately 8 for the biological sample. Based on the results, waxes showing SN ratios of 8 or higher in comparison with polyimide are qualified by the method explained above as waxes having a contrast imaging effect. These results indicate that it is possible to evaluate, using the polyimide tube instead of the biological sample, whether a candidate substance has an effect of a contrast agent.

TABLE 1

| Sample | Melting point | SN ratio |
| --- | --- | --- |
| Wax 1[a]-polyimide | 56-58° C. | 18.1 ± 1.1 |
| Wax 2[b]-polyimide | 56° C. | 18.8 ± 0.9 |
| Wax 3[c]-polyimide | 56-58° C. | 18.3 ± 1.2 |
| Wax 4[d]-polyimide | 58-60° C. | 17.6 ± 1.6 |
| Wax 5[e]-polyimide | 62-64° C. | 18.8 ± 1.3 |
| Polyethylene glycol-polyimide | 50-60° C. | 2.5 ± 0.4 |
| Wax 1-mouse kidney | 56-58° C. | 8.0 ± 1.1 |

Note:
[a] Paraffin deriving from a paraffin stick CT-PARA-ST manufactured by Genostaff Co., Ltd.
[b] Paraffin deriving from Paraplast Plus 502004 manufactured by McCormick Scientific Institute.
[c] Paraffin deriving from 24198-1 manufactured by Polysciences, Inc.
[d] Paraffin deriving from Parabet 60 manufactured by Muto Pure Chemicals Co. Ltd.
[e] Paraffin deriving from 24202-1 manufactured by Polysciences, Inc.

The invention claimed is:

1. A method of obtaining an X-ray CT image of a biological sample, the method comprising:
   penetrating a contrast agent into the biological sample and solidifying the contrast agent to provide a contrast image of the biological sample, the contrast agent comprising wax and having a density of 0.95 g/cm³ or less in its solidified state after penetration into the biological sample, and having a melting point of 40° C. to 80° C.;
   melting and resolidifying the solidified contrast agent; and
   acquiring an X-ray CT image by irradiating the resolidi- fied biological sample with an X ray having an energy of 4 to 12 keV, the shape of the biological sample being a shape with which a maximum optical path length of the X ray in the biological sample is 2 mm or less.

2. The method according to claim 1, wherein melting and resolidifying the contrast agent is performed in a state in which the biological sample is placed on a sample table.

3. The method according to claim 1, further comprising, before penetrating a contrast agent into the biological sample and solidifying the contrast agent to provide a contrast image of the biological sample, cutting the biologi- cal sample into a shape with which a maximum optical path length of the X ray in the biological sample is 2 mm or less.

4. The method according to claim 1, further comprising, after penetrating a contrast agent into the biological sample and solidifying the contrast agent to provide a contrast image of the biological sample, cutting the solidified bio- logical sample into a shape with which a maximum optical path length of the X ray in the biological sample is 2 mm or less.

5. The method according to claim 4, wherein cutting the biological sample is performed with a cylindrical pipe heated to a temperature higher than the melting point of the contrast agent.

6. The method according to claim 1, further comprising adding a marker to the biological sample, wherein
   acquiring an X-ray CT image includes correcting the X-ray CT image by moving slices of the X-ray CT image according to a movement of a projected marker image obtained from an X-ray projection image of the marker.

7. The method according to claim 1, wherein the contrast agent has a density of 0.95 g/cm³ or less at 25° C.

8. The method according to claim 1, wherein the wax is solid paraffin.

9. The method according to claim 1, wherein the X-ray CT image is clearly obtained with a voxel size of 5 μm or less.

10. A method of analyzing a biological sample, compris- ing:
    penetrating a contrast agent into a biological sample and solidifying the contrast agent to provide a contrast image of the biological sample, the contrast agent comprising wax having a density of 0.95 g/cm³ or less in its solidified state after penetration into the biological sample, and having a melting point of 40° C. to 80° C.;
    melting and resolidifying the solidified contrast agent;
    acquiring an X-ray CT image by irradiating the resolidi- fied biological sample with an X ray having an energy of 4 to 12 keV to acquire an X-ray CT image, the shape of the biological sample being a shape with which a maximum optical path length of the X ray in the biological sample is 2 mm or less;
    specifying a site to be further observed by an optical microscope and/or an electron microscope based on the acquired X-ray CT image and cutting and exposing the site;
    observing the site with the optical microscope and/or the electron microscope; and
    combining the X-ray CT image and results of the obser- vation by the optical microscope and/or the electron microscope to analyze the biological sample.

11. A contrast agent for X-ray CT of a biological sample, the contrast agent comprising wax and having a density of $0.95$ g/cm$^3$ or less in its solidified state after penetration into the biological sample, and having a melting point of 40° C. to 80° C.

\* \* \* \* \*